United States Patent [19]

Neustadt et al.

[11] 4,176,120

[45] Nov. 27, 1979

[54] 2-[4-(POLYHALO-2-HYDROXY-2-PROPYL-)ANILINO]THIAZOLIN-4-ONES

[75] Inventors: Bernard R. Neustadt, West Orange; Nicola Zampaglione, Fairfield, both of N.J.

[73] Assignee: Schering Corporation, Kenilworth, N.J.

[21] Appl. No.: 899,625

[22] Filed: Apr. 24, 1978

Related U.S. Application Data

[62] Division of Ser. No. 731,236, Oct. 12, 1976, Pat. No. 4,103,018.

[51] Int. Cl.$^2$ .......................................... C07D 277/04
[52] U.S. Cl. ....................................... 548/184; 424/270
[58] Field of Search ................................. 260/306.7 T

[56] References Cited

U.S. PATENT DOCUMENTS

| | | | |
|---|---|---|---|
| 4,071,528 | 1/1978 | Dalton et al. | 260/306.7 T |
| 4,081,547 | 3/1978 | Neustadt | 424/272 |
| 4,103,018 | 7/1978 | Neustadt et al. | 424/272 |

*Primary Examiner*—Nicholas S. Rizzo
*Attorney, Agent, or Firm*—Barbara L. Cowley Renda; Mary S. King; Bruce M. Eisen

[57] ABSTRACT

2-[4-(Polyhalo-2-hydroxy-2-propyl)anilino]-2-oxazolin-4-ones and the thiazolin-4-ones corresponding thereto, having useful anti-hypertensive properties, are disclosed herein. The compounds are prepared by reaction of the appropriate 4-(polyhalo-2-hydroxy-2-propyl)aniline with a β-chloroethanoyl isocyanate or isothiocyanate and then cyclization of the resultant intermediate.

6 Claims, No Drawings

2-[4-(POLYHALO-2-HYDROXY-2-PROPYL-)ANILINO]THIAZOLIN-4-ONES

This is a division of application Ser. No. 731,236, filed Oct. 12, 1976 now U.S. Pat. No. 4,103,018.

BACKGROUND OF THE INVENTION

2-[4-(polyhalo-2-hydroxy-2-propyl)anilino]-2-oxazolines are known as disclosed in copending application Ser. No. 668,385, filed Mar. 19, 1976, now U.S. Pat. No. 4,081,547 as useful agents for the treatment of hypertension. The art also discloses that substituted anilino-2-oxazolines have hypotensive activity, e.g., U.S. Pat. Nos. 3,453,284; 3,499,083; and 3,499,084; and Belgian Pat. Nos. 704,392; 704,393; and 704,396. However, these compounds lack the 4-one or 2-thiazolin-4-one functional group present in the compounds of this invention.

SUMMARY OF THE INVENTION

The present invention relates to novel 2-[4-polyhalo-2-hydroxy-2-propyl)anilino]-2-oxazolin-4-ones and thiazolin4-ones corresponding thereto which are useful in the treatment of mammalian hypertension. More particularly, this invention relates to compounds of the formula:

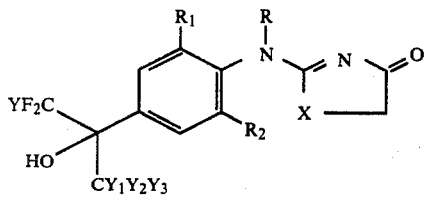

wherein X is oxygen or sulfur; R is hydrogen or lower alkyl; $R_1$ and $R_2$ are independently hydrogen, lower alkyl, lower alkoxy or halogen; and Y, $Y_1$, $Y_2$ and $Y_3$ are independently hydrogen, chlorine or fluorine.

The lower alkoxy groups referred to above contain 1 to 6 carbon atoms and are exemplified by such groups as methoxy, ethoxy, isopropoxy and the like.

The lower alkyl groups likewise contain 1 to 6 carbon atoms and are exemplified by methyl, ethyl, propyl, butyl, pentyl, hexyl and the corresponding branched chain isomers thereof.

The halogen atoms include fluorine, chlorine and bromine.

Within the scope of formula I there are certain preferential embodiments. R is preferably a lower alkyl group containing 1 to 4 carbon atoms. $R_1$ and $R_2$ are preferably hydrogen or a lower alkyl group. Y, $Y_1$, $Y_2$ and $Y_3$ are preferably selected so that at least two of them are fluorine.

Particularly preferred compounds of this invention are 2-[4-(hexafluoro-2-hydroxy-2-propyl)-N-methylanilino]-2-oxazolin-4-one and 2-[4-(hexafluoro-2-hydroxy-2-propyl-N-methylanilino]-2-thiazolin-4-one.

DETAILED DESCRIPTION OF THE INVENTION

The compounds of the present invention wherein X is oxygen are conveniently prepared by reaction of an aniline of the formula

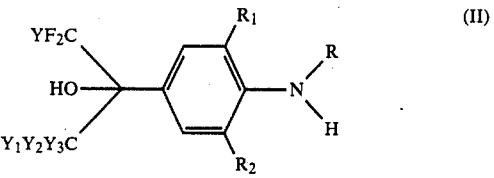

wherein R, $R_1$, $R_2$, Y, $Y_1$, $Y_2$ and $Y_3$ are as hereinbefore defined with chloroacetyl isocyanate to afford the intermediate of the formula

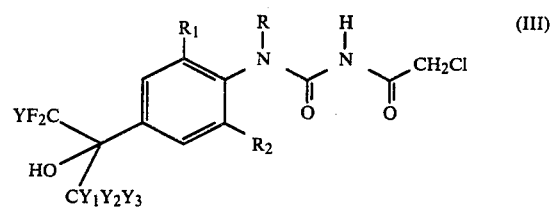

wherein R, $R_1$, $R_2$, Y, $Y_1$, $Y_2$ and $Y_3$ are as hereinbefore defined. If desired, the intermediate of formula III may be isolated. Cyclization of the intermediate of formula III affords the desired compound of formula I wherein X is oxygen. The cyclization step is preferably carried out using a base such as potassium t-butoxide. A particularly suitable solvent is dimethoxyethane, but others, such as diethoxyethane and tetrahydrofuran may also be used.

The above process is suitable for the manufacture of the following representative compounds of the invention:

2-[4-(hexafluoro-2-hydroxy-2-propyl)-N-methylanilino]-2-oxazolin-4-one;
2-[4-(hexafluoro-2-hydroxy-2-propyl)anilino]-2-oxazolin-4-one;
2-[4-(1,3-dichloro-1,1,3,3-tetrachloro-2-hydroxy-2-propyl)-N-methylanilino]-2-oxazolin-4-one;
2-[2,6-diisopropyl-4-(hexafluoro-2-hydroxy-2-propyl)-N-methylanilino]-2-oxazolin-4-one;
2-[4-(1,1,1-trifluoro-2-hydroxy-2-propyl)-N-methylanilino]-2-oxazolin-4-one;
2-[4-(chloropentafluoro-2-hydroxy-2-propyl)-N-methylanilino]-2-oxazolin-4-one;
2-[2,6-dichloro-4-(hexafluoro-2-hydroxy-2-propyl)-N-methylanilino]-2-oxazolin-4-one;
2-[2,6-diethyl-4-(hexafluoro-2-hydroxy-2-propyl)-N-methylanilino]-2-oxazolin-4-one;
2-[4-(hexafluoro-2-hydroxy-2-propyl)-2-methoxy-N-methylanilino]-2-oxazolin-4-one;
2-[2-fluoro-4-(hexafluoro-2-hydroxy-2-propyl)-N-methylanilino]-2-oxazolin-4-one;
2-[4-(hexafluoro-2-hydroxy-2-propyl)-2,6-dimethoxy-N-methylanilino]- 2-oxazolin-4-one; and
2-[N-ethyl-4-(hexafluoro-2-hydroxy-2-propyl)anilino]-2-oxazolin-4-one.

The compounds of the invention wherein X is sulfur are prepared in an analogous manner using chloroacetyl isothiocyanate in place of the chloroacetyl isocyanate. However, the cyclization occurs spontaneously to the hydrochloride salt of the thiazolin-4-one so that isolation of an intermediate corresponding to formula III is not possible.

Compounds of the present invention preparable by this method are:

2-[4-(hexafluoro-2-hydroxy-2-propyl)-N-methylanilino]-2-thiazolin-4-one;

2-[4-(hexafluoro-2-hydroxy-2-propyl)-N-ethylanilino]-2-thiazolin-4-one;

2-[N,2,6-trimethyl-4-(hexafluoro-2-hydroxy-2-propyl)anilino]-2-thiazolin-4-one; and 2-[4-(1,3-dichloro-1,1,3,3-tetrahydrofluoro-2-hydroxy-2-propyl)-N-methylanilino]-2-thiazolin-4-one.

Similarly, the other oxazolin-4-ones listed above have corresponding thiazolin-4-ones within the scope of this invention.

The 2-[4-(hexafluoro-2-hydroxy-2-propyl)-N-methylanilino]-2-oxazolin-4-one has been isolated from mammals treated with one of the corresponding deoxy compounds disclosed in copending application U.S. Ser. No. 668,385 and found to possess activity much greater than that of the compound of U.S. Ser. No. 668,385. Therefore, it is believed that the compounds of this invention are active metabolites of the corresponding deoxy compounds disclosed in copending application U.S. Ser. No. 668,385 and could be isolated from mammals which have been treated with the Ser. No. 668,385 compounds. In agreement with the isolated metabolite described above, the compounds of this invention display a marked increase in potency over the compounds of U.S. Ser. No. 668,385.

The compounds of formula I may be administered per se or in the form of their pharmaceutically acceptable acid addition salts. Exemplary of such salts are those formed with maleic, acetic, phthalic, succinic, lactic, tartaric, citric, malic, cinnamic, methanesulfonic, hydrochloric, hydrobromic, sulfuric and phosphoric acids. The salts may be prepared by the standard technique of precipitation by treatment of a solution of the free base in a suitable organic solvent with the desired acid. Further purification, if desired, may be effected by recrystallization.

The compounds of the present invention have been found to exhibit useful and potent anti-hypertensive activity. Based on laboratory tests, it is considered that the effective dose ($ED_{50}$) by oral administration for a compound of the present invention will typically lie within the range of 0.05 to 10 mg/kg of mammalian weight.

The required daily dosage may be administered in single or divided doses. The exact dose to be administered will, of course, be dependent upon various factors such as the particular compound employed, age and weight of the subject mammal and the individual's response.

The compounds are preferably and most advantageously administered orally. The compounds may be combined with any suitable pharmaceutical carrier and administered in a variety of formulations such as tablets, capsules, syrups, elixirs or suspensions.

Typical acceptable pharmaceutical carriers for use in formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate, polyvinylpyrrolidone; polyvinyl alcohol; stearic acid; alkaline earth metal stearates such as magnesium stearate and calcium stearate; stearic acid vegetable oils such as peanut oil, cottonseed oil, sesame oil, olive oil and corn oil; nonionic, cationic and anionic surfactants; ethylene glycol polymers; $\beta$-cyclodextrin; fatty alcohols; and hydrolyzed cereal solids; as well as other non-toxic compatible fillers, binders, disintegrants and lubricants commonly used in pharmaceutical formulations.

In treating certain patients with the compounds of this invention it may be desirable to include other pharmaceutically active ingredients in the same dosage unit. For example, in treating patients in whom salt and water retention is a problem, effective amounts of conventional diuretics can be incorporated, such as the thiazide diuretics can be incorporated, such as the thiazide diuretics, e.g., hydrochlorothiazide or trichloromethiazide. Similarly, in treating patients in whom tachycardia might be a problem, an effective amount of a pharmaceutically acceptable $\beta$-blocking agent can be included, e.g., propranolol. The dosage unit may even contain a combination of a compound of formula I, e.g., 2-[4-(hexafluoro-2-hydroxy-2-propyl)-N-methylanilino]-2-oxazolin-4-one, diuretic, e.g., hydrochlorothiazide, and a $\beta$-blocker, e.g., propranolol.

The following examples describe in detail representative compounds and compositions illustrative of the present invention. It will be apparent to those skilled in the art that many modifications, both of materials and methods, may be practiced without departing from the purpose and intent of this disclosure.

EXAMPLE 1

2-[4-Hexafluoro-2-Hydroxy-2-Propyl)-N-Methylaniline]-2-Oxazolin-4-One

To N'-methyl-N-chloroacetyl-N'-[4-(hexafluoro-2-hydroxy-2-propyl)phenyl] urea (3.93 gm., 0.01 mole) in dimethoxyethane (100 ml.), add potassium t-butoxide (2.24 gm., 0.02 mole) and stir for 30 minutes. Concentrate, add water (100 ml) and acidify with conc. HCl. Add sodium bicarbonate to neutrality and extract with ether. Dry the ether and concentrate. Triturate the crude product with ether. Filter off the precipitate, m.p. 225°–227° C.

EXAMPLE 2

2-[4-(Hexafluoro-2-Hydroxy-2-Propyl)-N-Methylanilino]-2-Thiazolin-4-One

To p-(hexafluoro-2-hydroxy-2-propyl)-N-methylaniline (2.73 gm., 0.01 mole) in dimethoxyethane (40 ml), add chloroacetyl isothiocyanate (1.50 gm., 0.011 mole) and stir 1 hr. Pour the reaction mixture onto water and neutralize with sodium bicarbonate. Extract with ether, dry and concentrate. Recrystallize from ether to obtain the product, m.p. 240°–242° C.

EXAMPLE 3

2-[4-(Hexafluoro-2-Hydroxy-2-Propyl)Anilino]-2-Oxazolin-4-One

To 1-(2-chloroacetyl)-3-[4-(hexafluoro-2-hydroxy-2-propyl)phenyl] urea (9.7 gm., 0.026 mole) in dimethoxyethane (500 ml) add potassium t-butoxide (5.7 gm., 0.051 mole). Stir 16 hr., concentrate, add water, acidify with conc. HCl, neutralize with sodium bicarbonate and extract with ether. Dry, concentrate, and recrystallize the residue from ether, to obtain the product, m.p. 272°–274° C.

EXAMPLE 4

| Tablet Formulations | |
|---|---|
| Formulation I | Milligrams per Tablet |
| 2-[4-(hexafluoro-2-hyroxy-2-propyl)-N-methylanilino]-2-oxazolin-4-one | 2 |
| Lactose, direct compression grade | 20 |
| Microcrystalline cellulose | 30 |
| Sodium Lauryl Sulfate | 20 |
| Corn starch | 25 |
| Magnesium stearate | 2 |
| | 300 |

Mix together the stated active ingredient, lactose, microcrystalline cellulose, sodium lauryl sulfate and corn starch. Pass through a No. 40 screen. Add the magnesium stearate, mix and compress into desired shape on a tablet machine.

| Formulation II | Milligrams per Tablet |
|---|---|
| 2[4-(hexafluoro-2-hydroxy-2-propyl)-N-methylanilino]-2-oxaxolin-4-one | 2 |
| Lactose, U.S.P. | 240 |
| Dicalcium phosphate | 56 |
| Sodium lauryl sulfate | 20 |
| Polyvinyl pyrrolidine | 10 |
| Water 50 ml/1000 tablets | |
| Corn starch | |
| Magnesium stearate | 2 |
| | 350 |

Mix together the stated active ingredient, lactose, dicalcium phosphate and sodium lauryl sulfate. Screen the above mixture through a No. 60 screen and granulate with an aqueous solution containing the polyvinyl pyrrolidone. Add additional water, if necessary, to bring the powders to a pasty mass. Add corn starch and continue mixing until uniform granules are formed. Pass through a No. 10 screen, tray and dry in an oven at 40° C. for 12 to 14 hours. Reduce the dried granulation through a No. 16 screen. Add the magnesium stearate, mix and compress into desired shape on a tablet machine.

EXAMPLE 5

| Capsule Formulation | |
|---|---|
| Ingredient | Milligrams per Capsule |
| 2-[4-(hexafluoro-2-hydroxy-2-propyl)-N-methylanilino]-2-oxazolin-4-one | 2 |
| Lactose, U.S.P. | 220 |
| Microcrystalline cellulose | 30 |
| Sodium lauryl sulfate | 20 |
| Corn starch | 25 |
| Magnesium stearate | 2 |
| | 300 |

Mix together the stated active ingredient, lactose, microcrystalline cellulose, sodium lauryl sulfate and corn starch. Pass through a No. 80 screen. Add the magnesium stearate, mix and encapsulate into the proper size two-piece gelatin capsule.

What is claimed is:

1. A compound of the formula

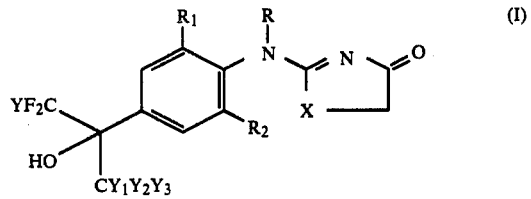

wherein X is sulfur; R is hydrogen or lower alkyl; $R_1$ and $R_2$ are independently hydrogen, lower alkyl, lower alkoxy or halogen; and Y, $Y_1$, $Y_2$ and $Y_3$ are independently hydrogen, chlorine or fluorine.

2. A compound according to claim 1 wherein Y, $Y_1$, $Y_2$ and $Y_3$ are fluorine.

3. A compound according to claim 2 wherein R is a lower alkyl group.

4. A compound according to claim 2 wherein $R_1$ and $R_2$ are both hydrogen.

5. A compound according to claim 2 wherein $R_1$ and $R_2$ are both lower alkyl groups.

6. The compound according to claim 1 which is 2-[4-(hexafluoro-2-hydroxy-2-propyl-N-methylanilino]-2-thiazolin-4-one.

* * * * *

UNITED STATES PATENT AND TRADEMARK OFFICE
CERTIFICATE OF CORRECTION

PATENT NO. : 4,176,120.
DATED : November 27, 1979.
INVENTOR(S) : Bernard R. Neustadt and Nicola Zampaglione.

It is certified that error appears in the above-identified patent and that said Letters Patent are hereby corrected as shown below:

Column 1, line 18, "4-one or 2-thiazolin-4-one func-" should read --4-one or 4-thione func---; column 3, line 7, "tetrahydrofluoro" should read --tetrafluoro--; column 4, lines 11-12, delete "such as the thiazide diuretics can be incorporated,"; column 4, line 21, "4-one, diuretic" should read --4-one, a diuretic--; column 5, line 7, "hyroxy" should read --hydroxy--; column 5, line 9, "20" should read --220--; column 5, line 25, "oxaxolin" should read --oxazolin--; column 5, line 30, insert --20-- horizontal with Corn Starch and vertically included in Milligrams per Tablet column.

Signed and Sealed this

Thirteenth Day of May 1980

[SEAL]

Attest:

SIDNEY A. DIAMOND

Attesting Officer

Commissioner of Patents and Trademarks